United States Patent
Pappas et al.

(10) Patent No.: US 7,279,280 B2
(45) Date of Patent: Oct. 9, 2007

(54) APPARATUS AND METHOD FOR DETECTING GENETIC MUTATIONS AND SINGLE NUCLEOTIDE POLYMORPHISMS

(75) Inventors: Michael Pappas, Lawrenceville, NJ (US); Zhuying Wang, Dayton, NJ (US)

(73) Assignee: MGP Biotech, Inc., Lawrenceville, NJ (US)

( * ) Notice: Subject to any disclaimer, the term of this patent is extended or adjusted under 35 U.S.C. 154(b) by 307 days.

(21) Appl. No.: 10/949,761

(22) Filed: Sep. 25, 2004

(65) Prior Publication Data

US 2005/0266419 A1    Dec. 1, 2005

Related U.S. Application Data

(60) Provisional application No. 60/509,015, filed on Oct. 6, 2003, provisional application No. 60/505,730, filed on Sep. 25, 2003.

(51) Int. Cl.
C12Q 1/68 (2006.01)
C07H 21/02 (2006.01)
C07H 21/04 (2006.01)

(52) U.S. Cl. ............... 435/6; 536/213.1; 536/24.3

(58) Field of Classification Search ............... 435/6; 536/23.1, 24.3
See application file for complete search history.

(56) References Cited

U.S. PATENT DOCUMENTS

| | | | |
|---|---|---|---|
| 4,988,617 A * | 1/1991 | Landegren et al. ............ | 435/6 |
| 5,352,578 A | 10/1994 | Agrawal et al. | |
| 5,436,327 A | 7/1995 | Southern et al. | |
| 5,559,221 A | 9/1996 | Agrawal et al. | |
| 6,048,695 A | 4/2000 | Bradley et al. | |
| 6,268,128 B1 | 7/2001 | Collins et al. | |
| 6,284,883 B1 | 9/2001 | Mills, Jr. | |
| 6,426,183 B1 | 7/2002 | Beattie | |
| 6,596,487 B2 * | 7/2003 | Raees et al. .................... | 435/6 |
| 6,773,884 B2 | 8/2004 | Mirkin et al. | |
| 6,777,186 B2 | 8/2004 | Mirkin et al. | |
| 2003/0129640 A1 * | 7/2003 | Sasaki et al. .................. | 435/6 |
| 2004/0005613 A1 * | 1/2004 | Norton .......................... | 435/6 |
| 2004/0035793 A1 * | 2/2004 | Legendre et al. ........... | 210/656 |
| 2004/0188254 A1 * | 9/2004 | Spaid .......................... | 204/451 |
| 2006/0008799 A1 * | 1/2006 | Cai et al. ....................... | 435/6 |
| 2006/0121452 A1 * | 6/2006 | Dhallan ......................... | 435/5 |

OTHER PUBLICATIONS

Anada, T. et al Anal. Sci. Jan. 2003; 19(1):73-7 Oligodeoxynucleotide-modified Capillary for Electrophoretic Separation of Single-Stranded DNAs with a Single-Base Difference.

* cited by examiner

Primary Examiner—Ethan Whisenant
(74) Attorney, Agent, or Firm—Altimatia, LLC; David M. Gange

(57) ABSTRACT

A method and means of identifying nucleic acid oligomers is disclosed. A sample is split into parts and the parts are flowed through chromatography columns containing nucleic acid oligomer probes bound to a binding medium. Analyte oligomers are transiently hybridized to complementary probe oligomers during chromatography. Detection and analysis of oligomer peaks is used to identify the oligomers contained in the sample.

15 Claims, 15 Drawing Sheets

Mutant Target Nucleic Acid Interaction with Different Probes

Mutant Column

```
                         SEQUENCE LISTING

<160> NUMBER OF SEQ ID NOS: 6

<210> SEQ ID NO 1
<211> LENGTH: 420
<212> TYPE: DNA
<213> ORGANISM: human

<400> SEQUENCE: 1
ccctggggca gaacacacac ggactcaaag agagggctg  acatctgtct gtgtgtctgt      60
ctgtccgtgt ctcccaggcc accccagagg agaagctcaa gctggaggac ttctttgccc     120
gcaactccta tgtggctggc cagtacgatg atgcagcctc ctaccagcgc ctcaacagcc     180
acatgaatgc cctccacctg gggtcacagg ccaaccgcct cttctacctg gccttgcccc     240
cgaccgtcta cgaggccgtc accaagaaca ttcacgagtc ctgcatgagc cagatgtaag     300
gcttgccgtt gccctccctt cccgcctgcc aggctggccc aggcagtgct cccaccactc     360
tatgagcgtg tccggggccg gggatctggg cagcatccat ggtgccgggg ccatccccag     420

<210> SEQ ID NO 2
<211> LENGTH: 11
<212> TYPE: DNA
<213> ORGANISM: human

<400> SEQUENCE: 2
gcatccatgt g                                                           11

<210> SEQ ID NO 3
<211> LENGTH: 10
<212> TYPE: DNA
<213> ORGANISM: human

<400> SEQUENCE: 3
```

```
                                                  -continued
gcacccatgt                                                                      10

<210> SEQ ID NO 4
<211> LENGTH: 11
<212> TYPE: DNA
<213> ORGANISM: human

<400> SEQUENCE: 4
gtccaggtac c                                                                    11

<210> SEQ ID NO 5
<211> LENGTH: 25
<212> TYPE: DNA
<213> ORGANISM: human

<400> SEQUENCE: 5
cagccacatc gatgccctcc acctg                                                     25

<210> SEQ ID NO 6
<211> LENGTH: 25
<212> TYPE: DNA
<213> ORGANISM: human

<400> SEQUENCE: 6
cagccacatg ggtgccctcc acctg                                                     25
```

APPARATUS AND METHOD FOR DETECTING GENETIC MUTATIONS AND SINGLE NUCLEOTIDE POLYMORPHISMS

This application claims the benefit of U.S. Provisional Patent Application Nos. 60/505,730 filed on Sep. 25, 2003, and 60/509,015 filed on Oct. 6, 2003. These applications are both hereby incorporated herein by reference.

A compact disk accompanying the application contains the file AL2004_11_SequenceListing.txt, which is 1,657 bytes in length, occupies 2048 bytes on disk, and was created on Sep. 23, 2004. The information contained within the file is hereby incorporated herein by reference.

BACKGROUND OF THE INVENTION

Genetic material, such as DNA and RNA from humans and other organisms, is often analyzed for nucleotide sequence, genetic-disease-causing mutations, or for single nucleotide polymorphisms (SNPs). Analysis often occurs after the DNA is isolated from cells and amplified using any of a number of amplification methods, such as the polymerase chain reaction (PCR), or the ligase chain reaction (LCR), among others. After DNA amplification, millions of identical copies of each DNA fragment are present in the sample fluid. These amplified fragments are then separated and concentrated into DNA bands containing fragments of identical length using either slab gel electrophoresis (SGE) or capillary gel electrophoresis (CGE).

A number of methods and instrument-based systems currently detect DNA sequences, genetic mutations, or SNPs after completion of DNA amplification and/or CGE or SGE. These include a number of DNA hybridization methods presently used in research protocols and in commercial assay systems. However, these systems have long assay times, require expensive reagents, and must be performed by highly trained technicians. In addition, some of these systems are not very sensitive and specific in detecting the presence of mutations or SNPs, particularly mutations involving stable mismatches. Finally, some of the methods are limited to low multiplex assays. In other words, the methods may only be used to analyze one, or at most a few nucleic acid fragments at a time.

An invention that quickly and efficiently determines the presence of mutations or SNPs, that minimizes cost, minimizes the use of technician time, and allows multiplex detection of many mutations at one time would be useful. In addition, it would also be useful to have a method that quickly identified nucleic acid sequences containing stable mismatches. Such a method would be of particular use in detecting nucleic acid mutations that result in genetic diseases.

SUMMARY

Various embodiments of the invention detect nucleic acid oligomers and oligomers containing mutations using a simple chromatographic process. Embodiments of the invention conduct affinity chromatography under conditions where hybridization and dissociation of oligomers and complementary molecules occur at nearly equal rates.

One embodiment of the invention is used for identifying specific nucleic acid oligomer sequences. A target oligomer sample is analyzed with the aid of a chromatographic binding medium. Probe oligomers are synthesized and attached to a chromatographic solid support forming the chromatographic binding medium. The probe oligomers comprise one oligomer complementary to the target wild-type oligomers of interest, a second oligomer complementary to target mutant oligomers of interest, and a third oligomer, acting as a control, that is not complementary to either the wild-type target oligomer or the mutant target oligomer. Chromatography columns are created using the chromatographic binding media. In one embodiment, each column contains a unique probe oligomer type. The sample to be analyzed is divided into parts, and each part is flowed down the chromatography columns using a buffer solution. The concentration of oligomer exiting the columns is monitored and the data are recorded. The passage of the target oligomer through the columns will be slowed in those columns containing probe oligomers that are complementary to the target oligomer, thereby indicating the identity of the target oligomer. Upon completion of the chromatography the columns may be flushed with buffer and reused.

Chromatographic binding is performed under conditions where the rates of hybridization and dissociation of target oligomers having a specific target sequence and probe oligomers having a sequence complementary to the target sequence is about the same. The dynamic hybridization-dissociation process can be described as transient hybridization. Transient hybridization conditions may be attained by conducting the chromatography at about the melting temperature of the double stranded complex consisting of the target oligomer and its' complementary probe oligomer.

Under transient hybridization conditions the drift rate of a target oligomer that is transiently hybridized by a probe oligomer will be slowed compared to the drift rate of an oligomer that is not transiently hybridized. For example, a target oligomer containing a wild-type sequence would be slowed on the column containing wild-type binding oligomers, but the drift rate would not be affected in the columns containing the mutant binding oligomers and control binding oligomers. Conversely, the drift rate of a target oligomer containing a mutant sequence would be slowed on the column containing mutant binding oligomers, but would not be slowed by the columns containing wild-type binding oligomers and control binding oligomers.

Upon completion of the analysis the columns are flushed to recondition them for further use. Each probe-oligomer-containing column may be used multiple times for the analysis of target oligomer samples.

The embodiments of the invention allow the detection of DNA or RNA nucleic acid oligomers and oligomers containing mutations. Several combinations of DNA and RNA nucleic acid target and nucleic acid probe oligomers may be used in the embodiments. Target RNA may be detected using DNA oligomer probes and conversely, target DNA can be detected using RNA oligomer probes. Further, target RNA may be detected using RNA oligomer probes and target DNA may be detected using DNA probes. Finally, synthetic oligomer probes prepared to have special properties, such as greater stability or increased resistance to DNAse or RNAse enzymes, may be used to detect DNA or RNA nucleic acid targets.

DETAILED DESCRIPTION

Figure 1:
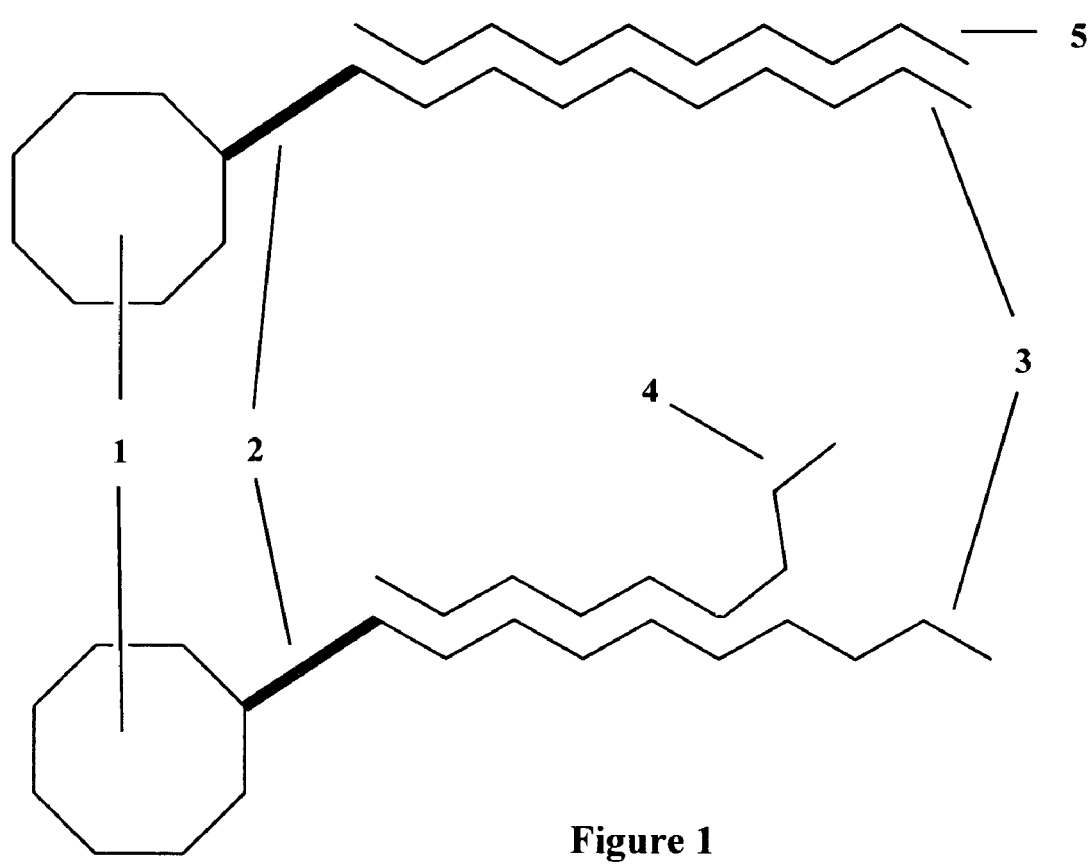
FIG. 1 is a schematic diagram showing binding medium with a solid support element (1) attached to a probe oligomers (3) via a linkers (2) having a binding interaction with a target oligomer (5) and a weak or non-binding interaction with a target oligomer (4).
Figure 2:
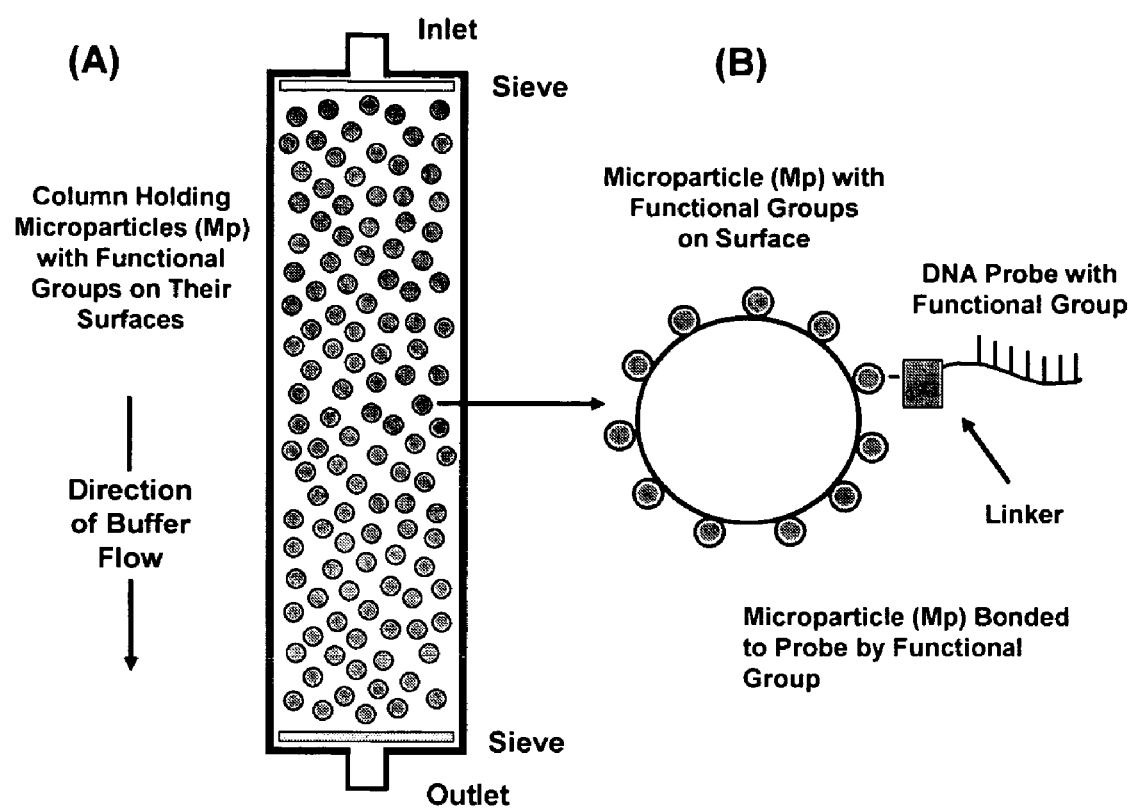
FIG. 2 is a schematic diagram showing a chromatography column (A) containing binding medium. A detail of a binding medium element is shown in FIG. 2B.

In describing embodiments of the present invention, specific terminology is employed for the sake of clarity. However, the invention is not intended to be limited to the specific terminology so selected.

Various embodiments detect nucleic acid oligomers and oligomer mutations using a simple chromatographic process.

Embodiments of the invention conduct affinity chromatography under conditions where hybridization and dissociation of oligomers and complements occur at nearly equal rates. For nucleic acid oligomers, the present embodiments include conducting the chromatography at or near the melting temperature of the double stranded complex comprising the oligomer and its complement.

Embodiments of the invention use a chromatographic binding medium having a solid support and binding oligomers possessing a subunit sequence complementary to at least a portion of an analyte target sequence. The solid support may be a chromatographic matrix such as beads, microbeads, or fibers that may be loaded into a chromatography column. The solid support may comprise a monolithic chromatographic matrix. The solid support may be made of silica gel, latex, polystyrene, polyvinyl, or other commonly used chromatographic medium. The binding oligomers may be covalently bound, or non-covalently bound to the solid support. The binding oligomers may be directly bound to the solid support or they may be bound to the solid support through a linker.

In general, target oligomers detectable by embodiments of the invention hybridize specifically to probe oligomers having complementary subunit sequences to form stable double-stranded complexes as depicted in FIGS. 1-5, 3A, 4B and 5A. Probe oligomers comprise from about 5 to about 30 nucleotides. The statement that a target oligomer hybridizes specifically to a probe oligomer is intended to mean that at least a portion of a target oligomer comprising a nucleotide sequence complementary to a sequence in a probe oligomer binds by Watson-Crick base-pairing to the complementary portion of the probe oligomer to form a stable double-stranded complex. The binding occurs under hybridization conditions that are sufficiently stringent that non-complementary target oligomers do not hybridize to form stable double-stranded complexes or do so with a rate of hybridization that is significantly less than the rate of dissociation as depicted in FIGS. 1-4, 3B, 3C, 4A, 4C, and 5C. Probe oligomers employed by embodiments of the invention may be modified to improve stability, resistance to degradation, binding affinity and other properties. Such modifications may include but are not limited to phosphorothioate modification, locked nucleic acid oligomers, and 2'-O-methyl modified oligoribonucleotides. The selection of parameters such as the lengths of the complementary portions of the different oligomers and of the conditions used in hybridization, e.g., the type of oligomer, concentration of oligomer and ionic strength of the solvent, so that the target oligomers hybridize specifically to their complementary probe oligomer counterparts are well known to persons of ordinary skill in the art.

Figure 6:
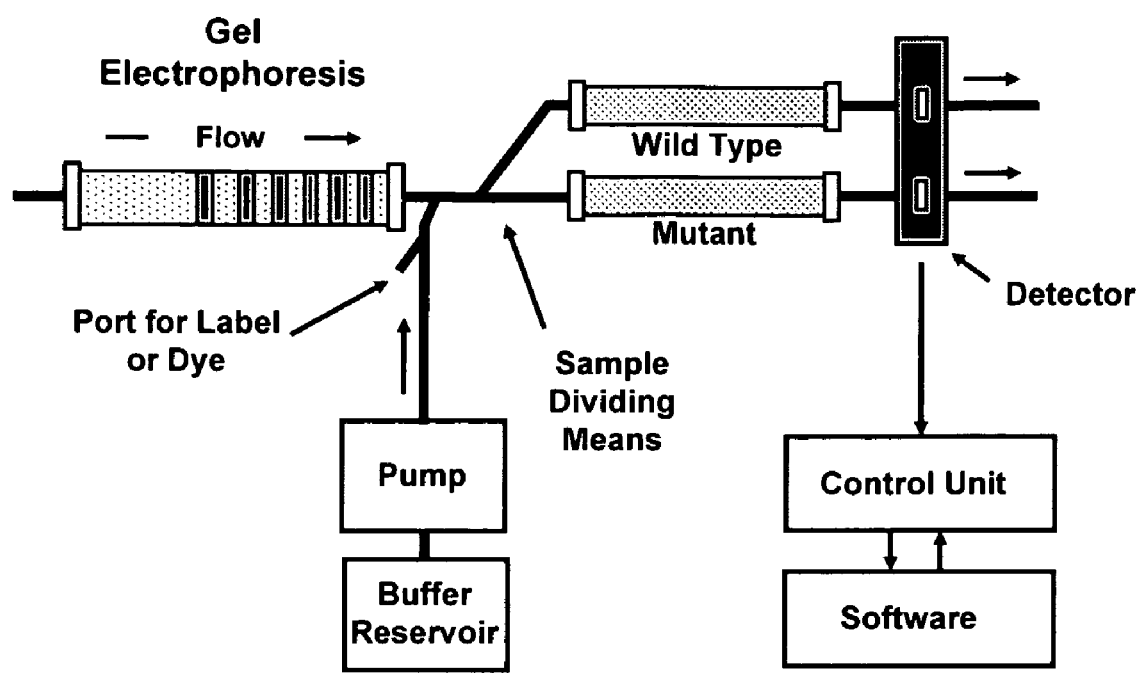
FIG. 6 is a schematic diagram depicting a two column apparatus used in one embodiment of the invention.
Figure 7:
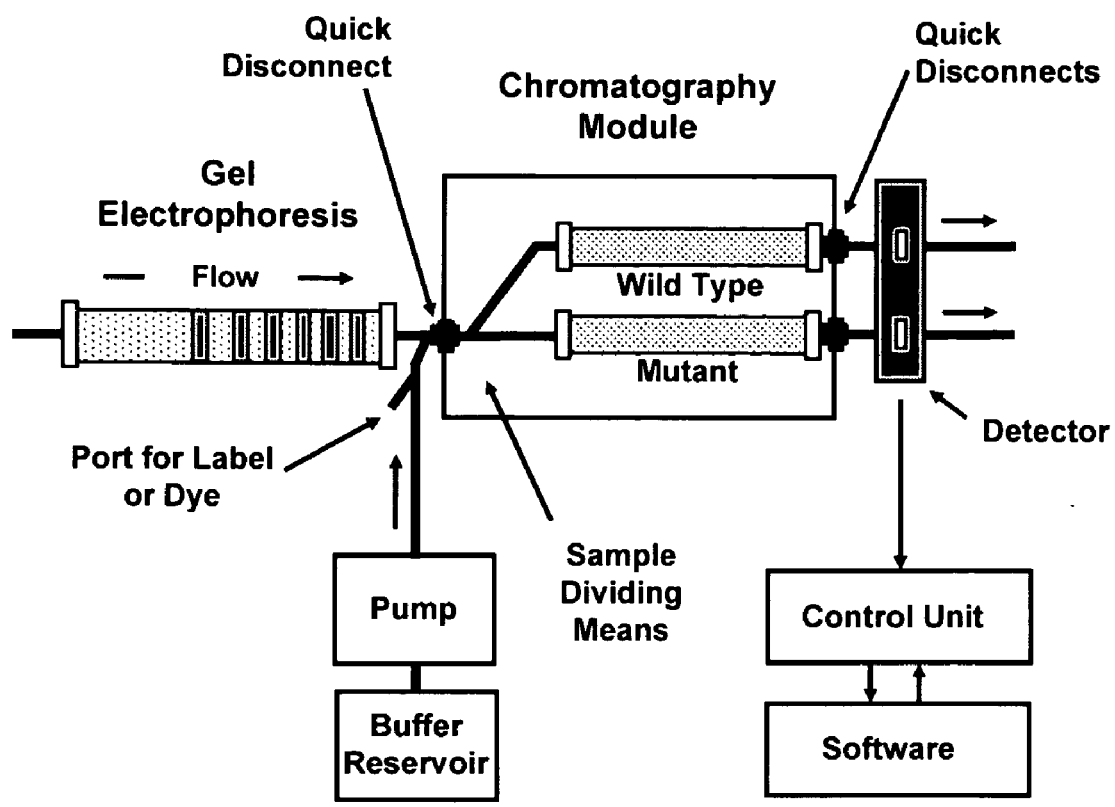
FIG. 7 is a schematic diagram depicting a modular two column apparatus used in one embodiment of the invention.
Figure 12:
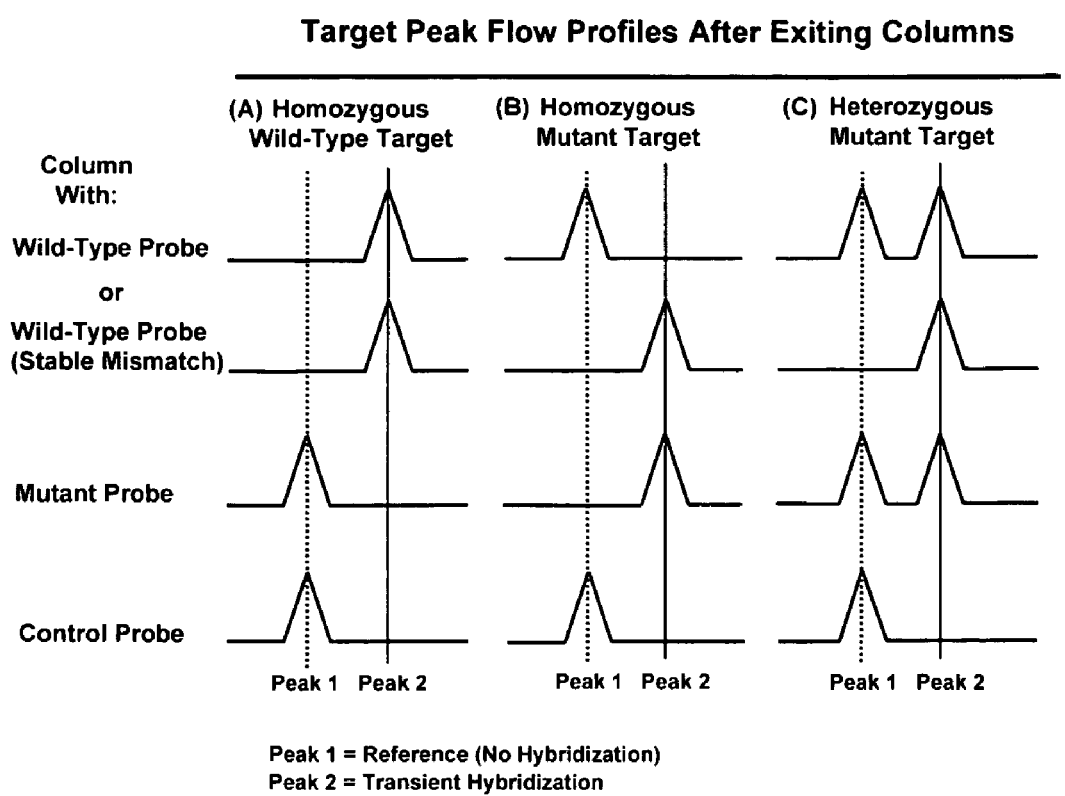
FIG. 12 is a schematic diagram depicting the peak profiles for homozygous and heterozygous targets that emerge from chromatography columns of the embodiments of the invention.

An embodiment of the invention to identify a single mutation is depicted in FIGS. 6 and 7. The embodiment works by first extracting a small volume of DNA from a subject. A single-stranded DNA (ssDNA) specimen derived from multiplex PCR using one phosphorothioate-modified primer and T7 exonuclease digestion is passed through a capillary gel electrophoresis (CGE) column that resolves ssDNA by length. Peaks exiting the CGE column provide target DNA for analysis. Target DNA sample is divided into two parts and placed on two columns containing binding medium. The binding medium in each column is comprised of different probe oligomers. One column contains a wild-type probe oligomer, a probe oligomer that is complementary to the wild-type target oligomer. A second column contains a mutant probe oligomer, a probe oligomer that is complementary to the mutant target oligomer of interest. The columns are used under conditions such that the rates of hybridization and dissociation of target oligomer to probe oligomer are about the same. The hybridization/dissociation rates can be adjusted by techniques that are well known to those of ordinary skill in the art. The oligomeric probe in the wild-type column will hybridize transiently to wild-type target DNA oligomers, slowing the movement of the wild-type oligomers through the column. The probe in the mutant column will hybridize transiently to mutant target DNA oligomers, slowing the movement of the mutant oligomers through the mutant column. If target DNA oligomers are homozygous wild-type or homozygous mutant then one peak will exit the columns. If the sample is heterozygous for the mutation then two sequential peaks will exit both the wild type column and the mutant column. The positions of target DNA oligomer peaks exiting the columns are compared. Peak number and peak position upon exiting each type of column will indicate whether the target DNA oligomers are homozygous wild-type, homozygous for a mutation, or heterozygous for a mutation as depicted in FIG. 12.

Flushing the columns upon completion of chromatography readies the columns for reuse.

Figure 8:
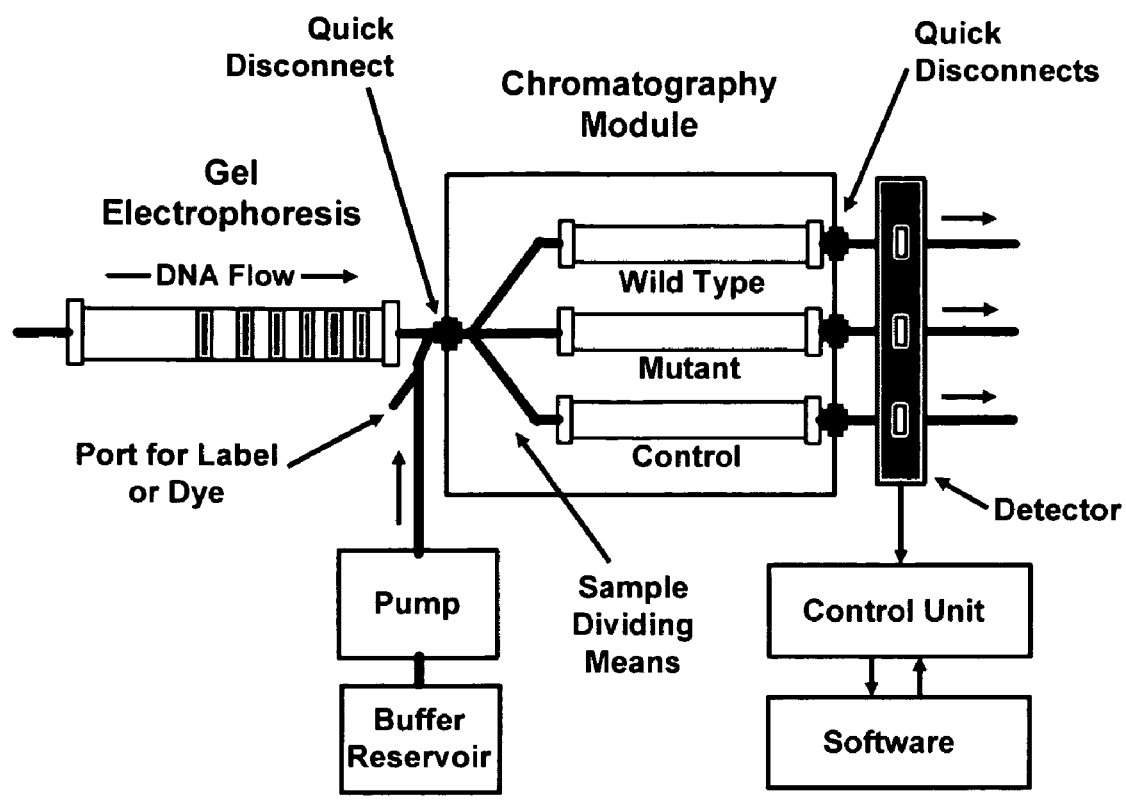
FIG. 8 is a schematic diagram depicting a modular three column apparatus used in one embodiment of the invention.
Figure 9:
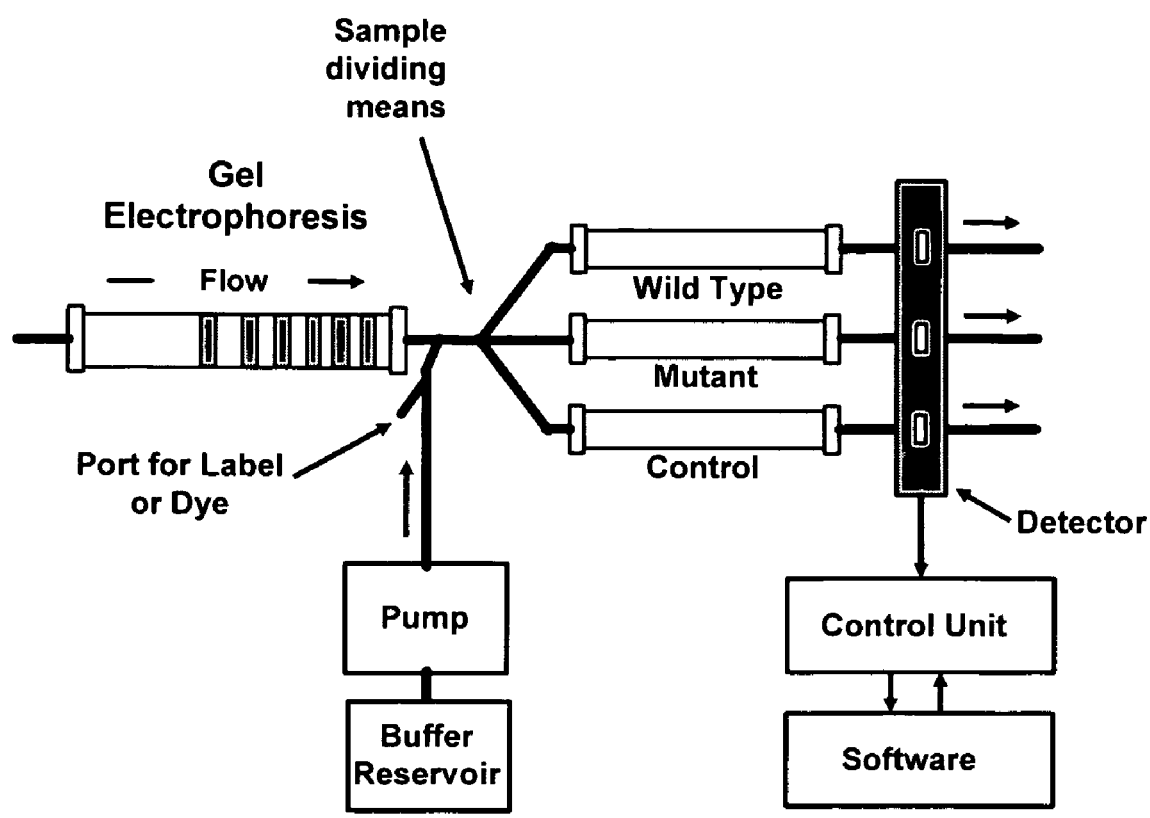
FIG. 9 is a schematic diagram depicting a three column apparatus used in one embodiment of the invention.

Another embodiment of the invention to identify a single mutation is depicted in FIGS. 8 and 9. The embodiment works by first extracting a small volume of DNA from a subject. A single-stranded DNA (ssDNA) specimen derived from multiplex PCR using one phosphorothioate-modified primer and T7 exonuclease digestion is passed through a capillary gel electrophoresis (CGE) column that resolves ssDNA by length. Peaks exiting the CGE column provide target DNA for analysis. Target DNA sample is divided into three parts and placed on three columns containing binding medium. The binding medium in each column is comprised of different probe oligomers. One column contains a wild-type probe oligomer, a probe oligomer that is complementary to the wild-type target oligomer. A second column contains a mutant probe oligomer, a probe oligomer that is complementary to the mutant target oligomer of interest. The third column contains a control probe oligomer, a probe oligomer that is designed to avoid complementing either the target wild-type oligomer or the target mutant oligomer. The columns are used under conditions such that the rates of hybridization and dissociation of target oligomer to probe oligomer are about the same. The hybridization/dissociation rates can be adjusted by techniques that are well known to those of ordinary skill in the art. The oligomeric probe in the wild-type column will hybridize transiently to wild-type target DNA oligomers, slowing the movement of the wild-type oligomers through the column. The probe in the mutant column will hybridize transiently to mutant target DNA oligomers, slowing the movement of the mutant oligomers through the mutant column. The control oligomeric probe in the control column is designed to avoid hybridizing either target wild-type or target mutant DNA. If target DNA oligomers are homozygous wild-type or homozygous mutant one peak will exit the columns. If the sample is heterozygous for the mutation then two sequential peaks will exit, both the wild type column and the mutant column. The positions of target DNA oligomer peaks exiting the columns are compared to the peak exiting the control column. Peak number and peak position upon exiting each type of column will indicate whether the target DNA oligomer is homozygous wild-type, homozygous for a mutation, or heterozygous for a mutation as depicted in FIG. 12. Flushing the columns upon completion of chromatography readies the columns for reuse.

Figure 5:
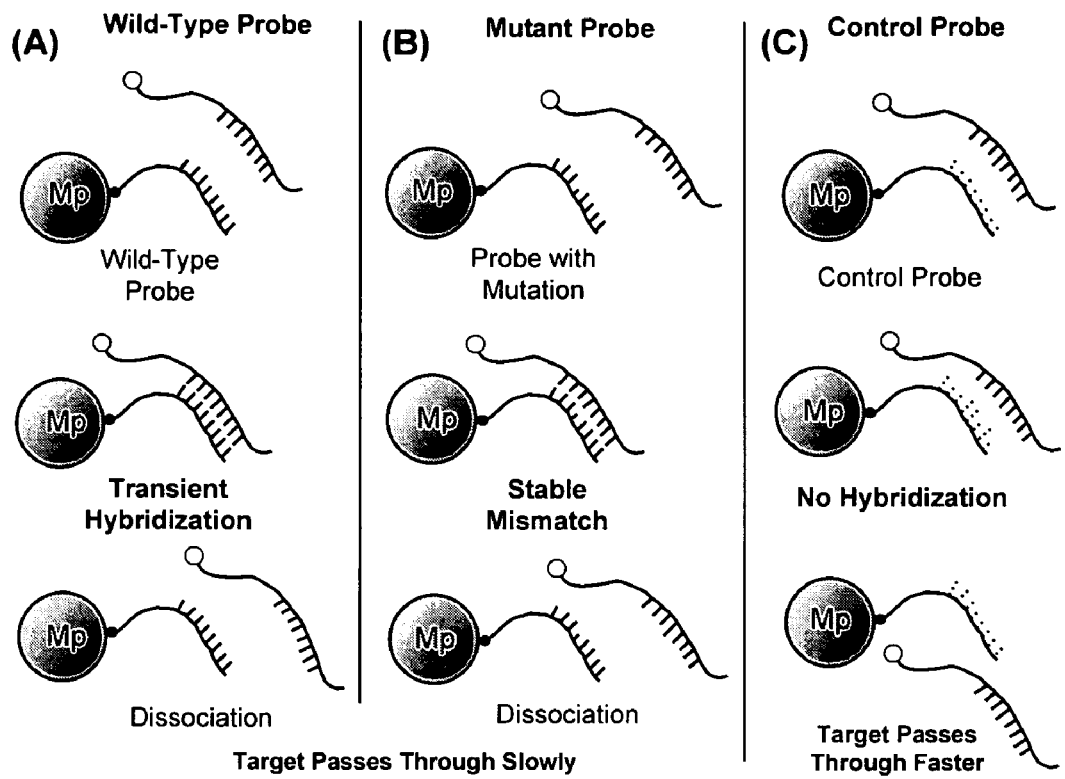
FIG. 5 is a schematic diagram showing the interaction of wild-type target oligomer, capable of forming a stable mismatch, with binding medium and wild-type (A), mutant (B), and control (C) probes.

Sometimes an oligomer probe's design causes it to hybridize to both a wild-type target oligomer and to a mutant oligomer in an assay. As depicted in FIG. 5, this special case occurs when a thermodynamically stable mismatch is involved, a common problem in hybridization assays. For example, a single G-T mismatch may be as stable as a true G-C match depending upon the nucleic acid sequence context. When analyzing oligomers using nucleic acid hybridization technology, stable mismatches can lead to false negative or false positive results. Transient hybridization identifies mutations and will display a distinct peak pattern even when stable mismatches are involved. A stable mismatch can only occur to one probe in an assay, either to wild-type or to mutant binding probes, but never to both at the same time, an important advantage of the embodiments of the invention.

Figure 3:
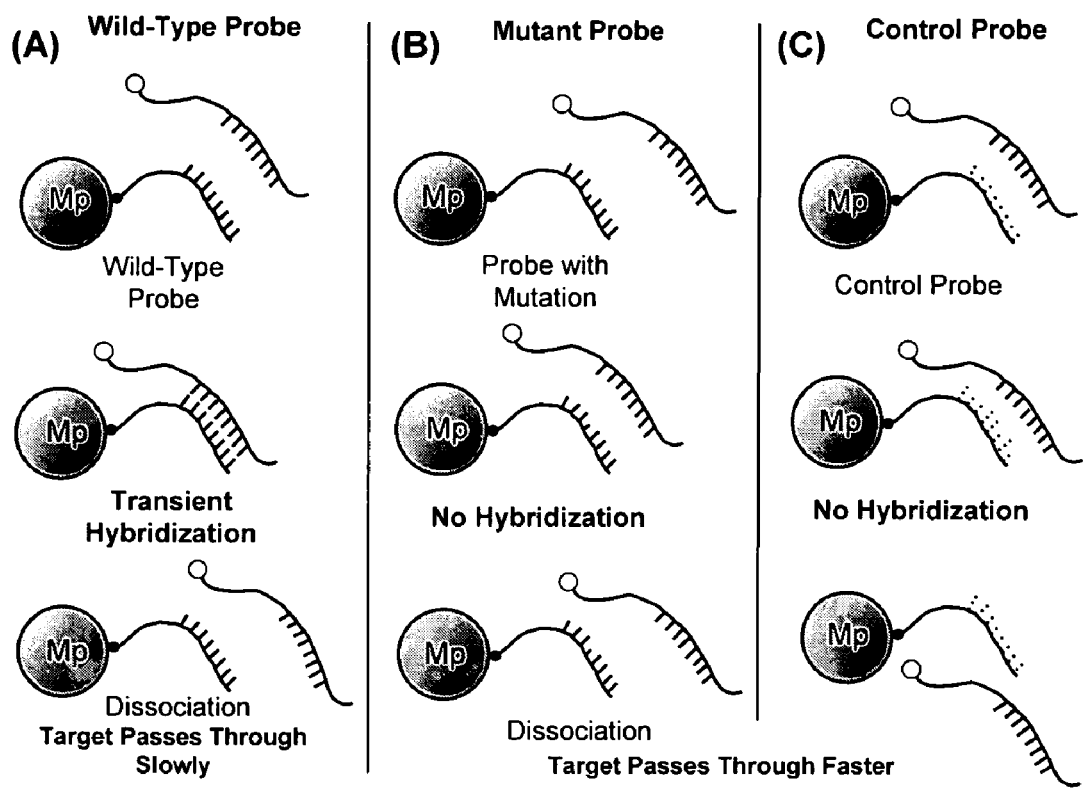
FIG. 3 is a schematic diagram showing the interaction of wild-type target oligomer with binding medium and wild-type (A), mutant (B), and control (C) probes.

As shown in FIGS. 3 and 12 the column containing the wild-type binding probe will cause a peak shift in the homozygous wild-type target oligomer, but no peak shift will be observed in oligomers exiting either the mutant binding probe column or the control binding probe column.

Figure 4:
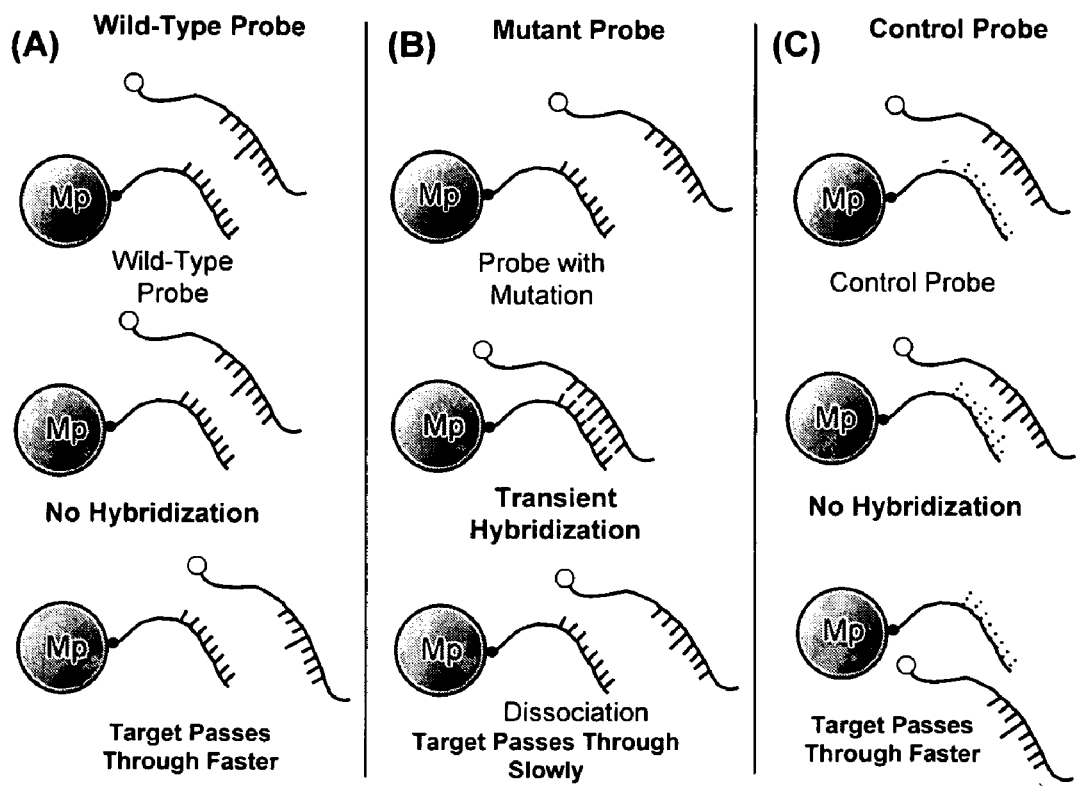
FIG. 4 is a schematic diagram showing the interaction of mutant target oligomer with binding medium and wild-type (A), mutant (B), and control (C) probes.

As shown in FIGS. 4 and 12 the column containing the mutant binding probe will cause a peak shift in the homozygous mutant target oligomer, but no peak shift will be observed in oligomers exiting either the wild-type binding probe column or the control binding probe column.

As shown in FIG. 12 both the column containing wild-type binding probe and the column containing the mutant binding probe will bind to a portion of a heterozygous sample resulting in two peaks being observed in each column, but no peak shift will be observed in oligomers exiting the control binding probe column.

In the special case of a stable mismatch involving the wild-type binding probe, as shown in FIGS. 5 and 12 the column containing wild-type binding probe will show a single shifted peak. The column containing the mutant binding probe will show a pair of peaks. No peak shift will be observed in the control binding probe column.

In the special case of a stable mismatch involving the mutant binding probe the column containing the mutant probe will show a single shifted peak and the column containing the wild type probe will show a pair of peaks, similar to the previous example. No peak shift will be observed in the control binding probe column.

Figure 10:
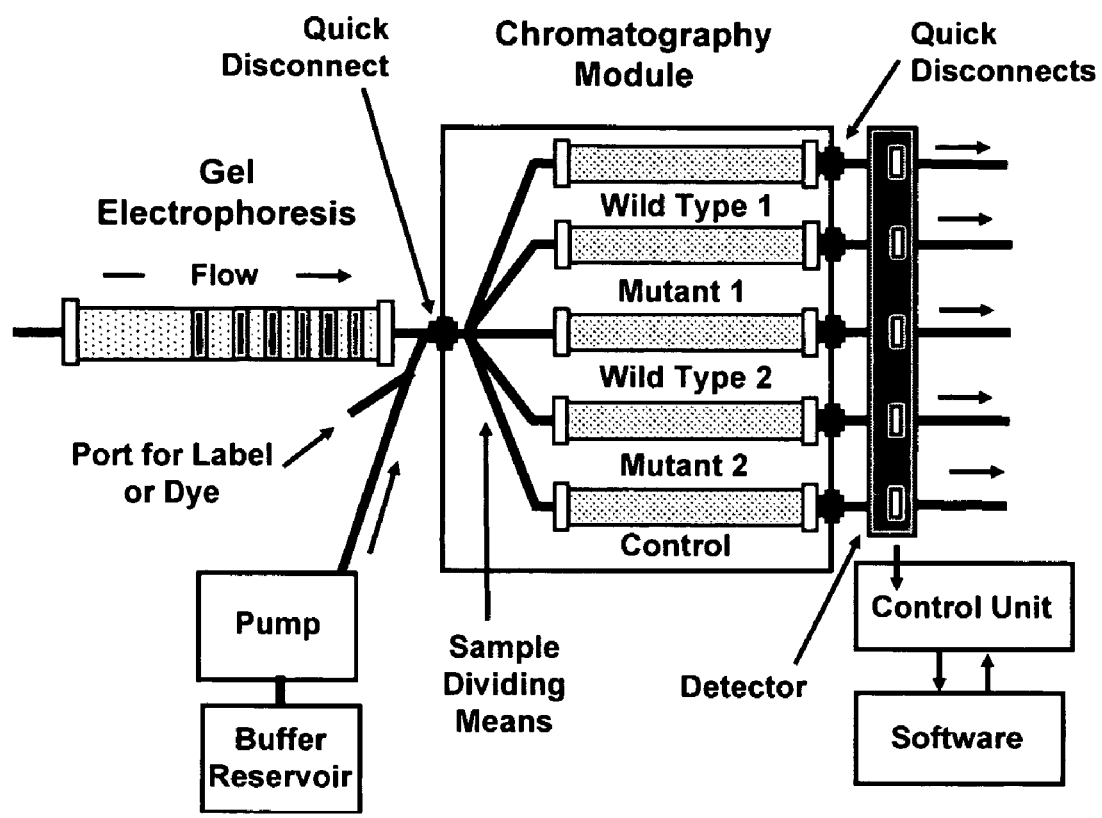
FIG. 10 is a schematic diagram depicting a modular five column apparatus used in one embodiment of the invention
Figure 11:
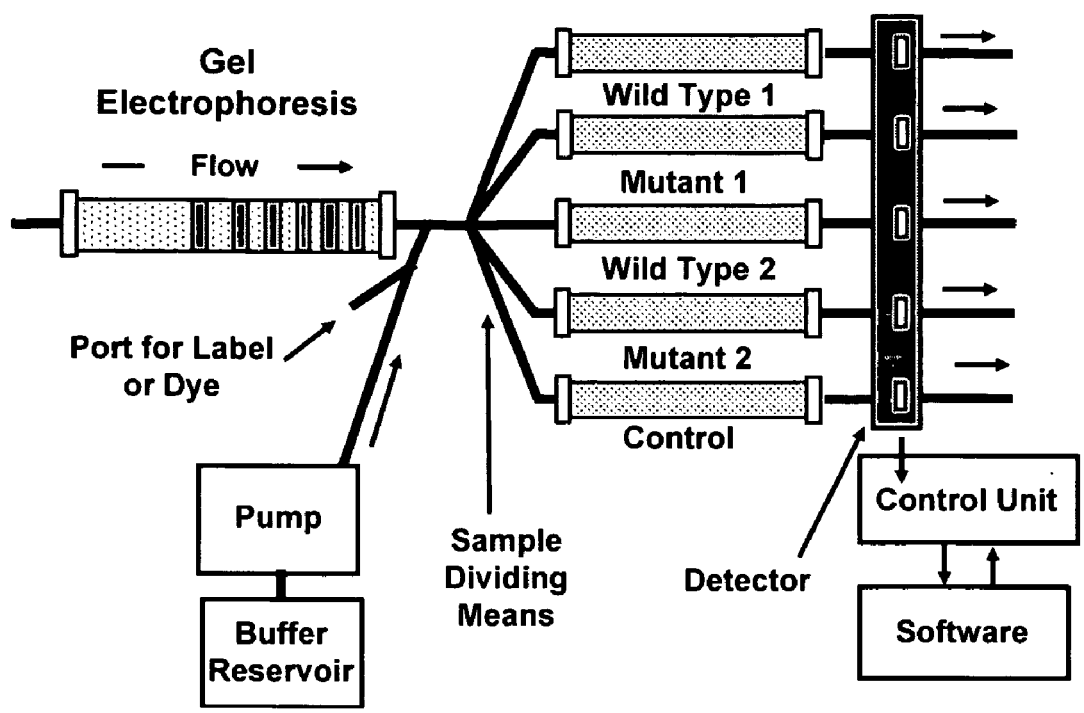
FIG. 11 is a schematic diagram depicting a five column apparatus used in one embodiment of the invention.

Another embodiment of the invention identifies multiple mutations and is depicted in FIGS. 10 and 11. The embodiment works by first extracting a small volume of DNA from a subject. A single-stranded DNA (ssDNA) specimen derived from multiplex PCR using one phosphorothioate-modified primer and T7 exonuclease digestion is passed through a capillary gel electrophoresis (CGE) column that resolves ssDNA by length.

Peaks exiting the CGE column provide target DNA for analysis. Target DNA sample is divided into multiple parts and placed on multiple columns containing binding medium. The number of columns will be determined by the number of mutations to be detected. Typically one control column is used and then for each mutation to be detected a wild-type column and a mutant column are used. The binding medium in each column is comprised of a different probe oligomer. One column contains a control probe oligomer, a probe oligomer that is designed to avoid complementing either the wild-type or the mutant target oligomers. The remaining columns are paired. For each mutation to be detected one column contains a wild-type probe oligomer, which is complementary to the wild-type target oligomer and a second column contains a mutant probe oligomer, which is complementary to the mutant target oligomer. The columns are used under conditions such that the rates of hybridization and dissociation of target oligomer to probe oligomer are about the same. The hybridization/dissociation rates can be adjusted by techniques that are well known to those of ordinary skill in the art. The oligomeric probes in the wild-type columns will hybridize transiently to wild-type target DNA oligomers, slowing the movement of the wild-type oligomers through the column. The probes in the mutant columns will hybridize transiently to mutant target DNA oligomers, slowing the movement of the mutant oligomers through the mutant columns. The control oligomeric probe in the control column is designed to avoid hybridizing to wild-type or mutant target DNA. A given target oligomer will typically be detected by a single pair of wild-type/mutant columns. If the target DNA oligomers are homozygous wild-type or homozygous mutant, one peak will exit the columns. If the sample is heterozygous for a mutation then two sequential peaks will exit both the wild type column and the mutant column of a particular pair of columns. The target DNA oligomer peaks exiting the columns are compared to the peak exiting the control column for positioning. Peak number and peak position upon exiting each type of column will indicate whether the target DNA oligomer is homozygous wild-type, homozygous for a mutation, or heterozygous for a mutation. Flushing the columns upon completion of chromatography readies the columns for reuse.

Another embodiment of the invention identifies multiple mutations and is depicted in FIGS. 8 and 9. The embodiment works by first extracting a small volume of DNA from a subject. A single-stranded DNA (ssDNA) specimen derived from multiplex PCR using one phosphorothioate-modified primer and T7 exonuclease digestion is passed through a capillary gel electrophoresis (CGE) column that resolves ssDNA by length. Peaks exiting the CGE column provide target DNA for analysis. Target DNA sample is divided into three parts and placed on three columns containing binding medium. The binding medium in each column is comprised of different probe oligomers. One column contains multiple wild-type probe oligomers, probe oligomers that are complementary to wild-type target oligomers. A second column contains multiple mutant probe oligomers, complementary to the mutant target oligomers. The wild-type and mutant oligomers are paired. For each mutation to be detected a wild-type oligomer is bound to the wild-type column and a mutant oligomer is bound to the mutant column. The probes on both the wild-type and mutant columns are selected so that they are not complementary to other probes located on the same column. The third column contains a control oligomer probe, designed to avoid complementing the target wild-type and target mutant oligomer sequences. The columns are used under conditions such that the rates of hybridization and dissociation of target oligomer to probe oligomer are about the same. The hybridization/dissociation rates can be adjusted by techniques that are well known in the art. The oligomeric probes in the wild-type column will hybridize transiently to wild-type target DNA oligomers, slowing the movement of the wild-type oligomers through the column. The probes in the mutant column will hybridize transiently to mutant target DNA oligomers, slowing the movement of the mutant oligomers through the mutant column. The control oligomeric probe in the control column is designed to avoid hybridizing wild-type and mutant target DNA. If target DNA oligomers are homozygous wild-type or homozygous mutant, one peak will exit the columns. If the sample is heterozygous for the mutation then two sequential peaks will exit both the wild type column and the mutant column. The target DNA oligomer peaks exiting the columns are compared to the control column for positioning. Peak number and peak position upon exiting each type of column will indicate whether the target DNA oligomer is homozygous wild-type, homozygous for a mutation, or heterozygous for a mutation. Flushing the columns upon completion of chromatography readies the columns for reuse.

In the preceding embodiments PCR was used to provide nucleic acid samples for analysis. In addition to PCR, LCR, nested PCR may be used. Nucleic acids produced by other means, such as purification from cells or cellular components, such as mitochondria, may also be used.

In the preceding embodiments slab gel electrophoresis and other nucleic acid purification techniques may be used in place of capillary gel electrophoresis to provide target nucleic acid samples for analysis.

In some of the preceding embodiments a column comprising control probes was employed to provide an external standard for use in the analysis of the oligomer peak profile data. An internal standard, comprising an unlabeled or labeled nucleic acid oligomer may be employed in embodiments of the invention. Such internal standards are placed upon chromatography columns of embodiments of the invention together with the sample to be analyzed. Internal standards are designed such that their nucleotide sequences are not complementary to the probe sequences of the columns on which they are placed.

In the preceding examples the detection of the target nucleic acid oligomer peaks exiting the columns may be accomplished by several methods well known to those of ordinary skill in the art including UV/VIS spectroscopy, infrared spectroscopy, mass spectrometry, fluorescence detection, chemiluminescence detection, nuclear magnetic resonance detection, and radiometric detection is radio isotopes. The detection of the target oligomers may be enhanced through modification of the oligomers by the covalent or non-covalent attachment of fluorescent dyes such as dimeric cyanine stains TOTO-1, YOYO-1, and OliGreen (reagent available from Molecular Probes), radio isotopes such as radioactive hydrogen, radioactive phosphorus, radioactive iodine, lanthanides, enzymes such as alkaline phosphatase or horseradish peroxidase, and other nucleic acid labeling techniques which are well known to those skilled in the art.

An embodiment of the invention may be used to detect cystic fibrosis. Cystic fibrosis (CF) is a highly morbid, autosomal recessive disease caused by one or more mutations in the gene encoding for the cystic fibrosis transmembrane conductance regulator (CFTR) protein. The CFTR gene is located on chromosome 7 at position 7g31.2. In the Caucasian population CF is inherited with a frequency of 1:3,300, making it the most lethal inherited disease of childhood. A single mutation (ΔF508) accounts for about 70% of all mutations observed in Caucasians with CF, but over 1,000 other mutations to the CFTR gene have been reported in all races and ethnic groups. Some mutations are observed mainly in Caucasians, others are more common in African Americans or in Hispanics. About 20 of these mutations are relatively common in the world population.

Genetic screening has demonstrated a large number of mutations leading to CF in different races and ethnic groups. A single mutation panel chosen for Caucasians and Ashkenazi Jews detects from 80-97% of CF carriers but detects fewer CF carriers in African Americans and Hispanics. This is because certain mutations are associated with specific groups of people. Common African mutations can identify an additional 23% of CF patients. When these sets of mutations were used together, the combined CF detection rate is similar to that observed in Caucasian CF patients. Other mutations specific for ethnic groups have been reported.

Sensitive and specific detection of gene mutations using embodiments of our invention include but are not limited to common mutations of the CFTR gene: ΔF508; 3120+1 G->A; 3876delA; R553X; G542X; 405+3A->C; A559T; G551D; N1303K; W 1282X, as well as less common mutations, such as 3622insT and 3601-20T->C. Preparation and optimization of oligomer probes to these mutations as well as to the corresponding wild-type sequences may be accomplished by techniques that are well known in the art. Such oligomer probes may be used to transiently bind to either wild-type DNA or mutant DNA as previously described. Detection of peaks may be performed using techniques previously described and by other methods and techniques which are well known in the art.

An embodiment of the invention may be used to detect muscular dystrophy. The muscular dystrophies (MD) are a group of genetic diseases characterized by progressive weakness and degeneration of the skeletal muscles which control movement. The three most common types of MD are Duchenne, facioscapulohumeral, and myotonic. These three types differ in terms of pattern of inheritance, age of onset, rate of progression, and distribution of weakness.

Of these, Duchenne Muscular Dystrophy (DMD) is an inherited disorder caused by a mutation in the gene that produces dystrophin. The dystrophin gene maps to chromosome X (Xp21.2). This mutation is passed down from mother to son because the dystrophin gene is located on the X chromosome. Sons will develop DMD because they have only one copy of the X chromosome. Females have two X chromosomes, so they may inherit a normal copy of the DMD gene from their father. Females with a defective gene for dystrophin are carriers and can pass DMD on to their sons.

Sensitive and specific detection of gene mutations using our embodiment include but are not limited to the five most common mutations of the dystrophin gene: CTG trinucleotide repeat; DGS654A; 3359 C->T; 738+1 G->T, as well as other less common mutations. Preparation and optimization of oligomer probes to these mutations as well as to the corresponding wild-type sequences may be accomplished by techniques that are well known in the art. Such oligomer probes may be used to transiently bind to either wild-type DNA or mutant DNA as previously described. Detection of peaks may be performed using techniques previously described and by other methods and techniques which are well known in the art.

An embodiment of the invention may be used to detect BRCA1 linked breast cancer. Breast cancer is an important cancer of women. Around 180,000 women and some men are diagnosed with breast cancer each year. BRCA1 mutations affect about five percent of these cases. These are familial, early-onset cancers. BRCA1 mutations are linked to ovarian cancer as well (4% of all female cancers). BRCA1 is a tumor suppressor gene located on the long arm of chromosome 17q21. This gene may play a role in regulating cell growth. Inheriting a mutant copy of BRCA1 predisposes a woman to breast or ovarian cancer. Development of cancer in either organ involves a number of additional mutations, at least one of which involves the other copy (allele) of BRCA1.

Sensitive and specific detection of gene mutations using our embodiment include but are not limited to the following mutations of the BRCA1 gene: G1710X; IVS5+3A->G; 2478-2479insG; 1135delA; E1221X; 5382insC; 185delAG, and; 3600del11 (exon 11). Preparation and optimization of oligomer probes to these mutations as well as to the corresponding wild-type sequences may be accomplished by techniques that are well known in the art. Such oligomer probes may be used to transiently bind to either wild-type DNA or mutant DNA as previously described. Detection of peaks may be performed using techniques previously described and by other methods and techniques which are well known in the art.

An embodiment of the invention may be used to detect familial hypercholesterolemia. Familial hypercholesterolemia (FH) is caused by mutations in the gene encoding apolipoprotein B-100 (apoB), affecting one in 500 individuals. A component of cholesterol called apolipoprotein B may be strongly linked to several heart disease risk factors and may be a better predictor of cardiovascular disease risk than low-density lipoprotein (LDL) cholesterol.

People with normal LDL and elevated apoB are more likely to have abdominal obesity, high blood insulin levels and clotting factors compared to people with high LDL and normal apoB levels. All of these factors also contribute to the metabolic syndrome.

Sensitive and specific detection of gene mutations using our embodiment include but are not limited to the following mutations of the apoB gene: 3500Q, and; 3531. Preparation and optimization of oligomer probes to these mutations as well as to the corresponding wild-type sequences may be accomplished by techniques that are well known in the art. Such oligomer probes may be used to transiently bind to either wild-type DNA or mutant DNA as previously described. Detection of peaks may be performed using techniques previously described and by other methods and techniques which are well known in the art.

Another embodiment of the invention may also be used to detect familial hypercholesterolemia. Familial hypercholesterolemia (FH) is a hereditary metabolic disorder caused by mutations in the low-density lipoprotein receptor (LDLR) gene. FH is characterized by high levels of low-density lipoprotein cholesterol and an extreme risk of premature cardiovascular disease. Affected people have consistently high levels of low-density lipoprotein, which leads to premature atherosclerosis of the coronary arteries. The LDLR gene is located at 19p13.2. Mutations in this gene cause the FH phenotype. In patients with heterozygous familial hypercholesterolemia a substantial variation is seen in both the severity of the hypercholesterolemia and onset of atherosclerotic disease symptoms.

Sensitive and specific detection of LDLR gene mutations using our embodiment include but are not limited to the following mutations of the LDL receptor gene: C6W; S265R; A370T; Q363P; D365E; V408M; A410T; A517T; G528D; G571E; Q363X and C660X; 2140+5G->A; 2140+9C-->T; 1706-10G->A; −45delT; G197del; E397X; c.1957G->T; p.V653F, c.647 G->A; p.C216Y; c.1-156 C->T (in repeat 2 of the promoter region) c.1060+10C->G; c.1171G->A; c. 117 C/T; p.A391T; p.V653F; c.1150C->T; p.Q384X; c.1158C->G; c.447 T->C; c.1171 G/A; c.1413 G/A; c.1545 C/T; 1773 T/C; 1959 C/T; 2231 G/A; p.D386E. Preparation and optimization of oligomer probes to these mutations as well as to the corresponding wild-type sequences may be accomplished by techniques that are well known in the art. Such oligomer probes may be used to transiently bind to either wild-type DNA or mutant DNA as previously described. Detection of peaks may be performed using techniques previously described and by other methods and techniques which are well known in the art.

An embodiment of the invention may be used to detect sickle cell anemia. Sickle cell anemia affects millions of people worldwide. It is very common among people whose ancestors come from sub-Saharan Africa; Spanish-speaking regions (South America, Cuba, Central America); Saudi Arabia; India; and Mediterranean countries. In the United States, it affects around 72,000 people, most of whose ancestors come from Africa. The disease occurs in about 1 in every 500 African-American births and 1 in every 1,000 to 1,400 Hispanic-American births. About 2 million Americans, or 1 in 12 African Americans, carry the sickle cell trait. If each parent carries one sickle hemoglobin gene (S) and one normal gene (A), each child has a 25% chance of inheriting two defective genes and having sickle cell anemia.

The HBB gene is found at 11p15.5. Although several hundred HBB gene variants are known, sickle cell anemia is most commonly caused by the hemoglobin variant Hb S.

The A->T mutation at the 17th nucleotide of HBB gene open reading frame causes sickle cell anemia (Hb S). In this variant, the hydrophobic amino acid valine takes the place of hydrophilic glutamic acid at the sixth amino acid position of the HBB polypeptide chain. Normal red blood cells are smooth and round like doughnuts. In sickle cell anemia, the red blood cells become hard, sticky, and shaped like sickles or crescents. When these red cells travel through small blood vessels, they often get stuck and block the flow of blood. This causes pain, damage, and a low blood count or anemia. While normal red blood cells last about 120 days in the bloodstream but sickle cells are removed from the bloodstream after only about 10 to 20 days.

Sensitive and specific detection of gene mutations using our embodiment include but is not limited to the single point mutation of amino acid 6 from glutamic acid to valine of the HBS gene. Preparation and optimization of oligomer probes to these mutations as well as to the corresponding wild-type sequences may be accomplished by techniques that are well known in the art. Such oligomer probes may be used to transiently bind to either wild-type DNA or mutant DNA as previously described. Detection of peaks may be performed using techniques previously described and by other methods and techniques which are well known in the art.

As depicted in FIGS. 6-11 an apparatus for performing embodiments of the invention comprise the following elements: source of target nucleic acids, such as gel electrophoresis; optional source of nucleic acid label such as fluorescent dye or other label; injection port for the optional nucleic label and optional internal standard; reservoir of buffer; pump or pumps; sample dividing means such as a splitting junction or valve or automated sampler or other means of dividing a sample well known to those of ordinary skill in the art; chromatography columns containing binding medium; oligomer detection apparatus; control unit apparatus and software for receiving, analyzing, and storing information coming from the detection apparatus. In addition to analyzing data received from the detector, the control unit apparatus may also receive data from and control the actions of the other elements of the system including the reservoir, pumps, valves, sample inlet system, label injection system, and dividing means. The chromatography columns may be comprise a module which may form a portion of a larger apparatus. The module may optionally comprise a dividing means for dividing the sample between the columns.

Experimental Results

Glucose-6-phosphate dehydrogenase (G6PD) deficiency is the most prevalent enzymopathy in humans. The disease affects about 400 million individuals worldwide, causing a number of hemopathies, triggered by certain antibiotics, foods or pathogens, most often in males. However, hemolytic episodes in affected females are underreported. The 376 A to G mutation is an important mutation in G6PD deficiency. The sequence flanking the mutation is shown below (Seq ID 1):

```
376 A→G (aa 126)
14041  ccctggggca gaacacacac ggactcaaag agagggctg acatctgtct gtgtgtctgt 14101  ctgtccgtgt ctcccaggcc acccagagg agaagctcaa gctggaggac ttctttgccc 14161  gcaactccta tgtggctggc cagtacgatg atgcagcctc ctaccagcgc ctcaacagcc 14221  acatgaatgc cctccacctg gggtcacagg ccaaccgcct cttctacctg gccttgcccc 14281  cgaccgtcta cgaggccgtc accaagaaca ttcacgagtc ctgcatgagc cagatgtaag 14341  gcttgccgtt gccctccctt cccgcctgcc aggctggccc aggcagtgct cccaccactc 14401  tatgagcgtg tccggggccg gggatctggg cagcatccat ggtgccgggg ccatccccag
```

The binding probes shown below were designed to have the same melting temperature (Tm) using a TM calculation package called HyTherm (available from Dr. Santa Lucia, Wayne State University, Detroit, Mich.).

The following probe sequences were prepared by standard techniques well known to those of ordinary skill in the art:

```
G6PD Probe Sequences
Wild-type probe: 5'-NH2-GCA TCC ATG TG-3'  Tm: 40.2° C. (Seq ID 2)

Mutant probe:    5'-NH2-GCA CCC ATG T-3'   Tm: 40.1° C. (Seq ID 3)

Control probe:   5'-NH2-GTC CAG GTA CC-3'  Tm: 40.6° C. (Seq ID 4)
```

Synthetic G6PD target DNA oligomers with Cy3 fluorescent dye attached at the 5' end were prepared according to procedures that are well known in the art. The sequences are listed below:

```
Wild-type target 5' CAG CCA CAT CGA TGC CCT CCA CCT G-3' (Seq ID 5)

Mutant target    5' CAG CCA CAT GGG TGC CCT CCA CCT G-3' (Seq ID 6)
```

The purity of the target oligomers was confirmed via gel electrophoresis.

Preparation of Probe-Coupled Microbeads

Microbeads with amino groups from a commercial source were added to 1.5 ml polypropylene Eppendorf tubes and washed 3 times (centrifugation followed by pipeting off supernatant) with 10% pyridine in dimethylformamide (DMF) to remove fines. The microbeads were stored at 4° C.

One day prior to use 100 mg of amino-derivatized polymeric microbeads were reacted with 1.5 ml of 10 succinic anhydride in pyridine:DMF (1:9) in a 1.5 ml Eppendorf tube. The reaction mixture was rotated at 25 rpm at room temperature (25° C.) for one hour on a tube rotator (Glas Col, Terre Haute, Ind.) to yield conditioned microbeads. The conditioned polymeric microbeads were washed with 800 µl of DMF two times at room temperature, and then transferred to a new tube. The conditioned polymeric microbeads were washed twice more with DMF and then washed twice with 800 µl of distilled H2O (centrifugation followed by pipeting off supernatant).

To 100 mg of conditioned microbeads was added 800 µl of 20 mM 1-(3-Dimethylaminopropyl)-3-ethycarbodiimide Hydrochloride (EDC) in 0.1 M 2-(N-morpholino)-ethanesulfonic acid (MES) buffer (pH about 4.5) with mixing, followed immediately by 100 µl of 100 µM 5'-amino-modified oligonucleotide probe in distilled water. The mixture was reacted for 30 minutes to yield low-density, probe-coupled, polymeric microbeads. The microbeads were washed five times with 1 ml running buffer to give the purified microbead binding medium. The microbead binding medium was then packed into a chromatography column.

To 50 mg of conditioned microbeads was added 800 µl of 20 mM EDC in 0.1 M MES buffer (pH about 4.5) with mixing, followed immediately by 100 µl of 100 µM 5'-amino-modified oligonucleotide probe in distilled water. The mixture was reacted for 3 hours to yield high-density, probe-coupled, polymeric microbeads. The microbeads were washed five times with 1 ml running buffer to give the purified microbead binding medium. The microbead binding medium was then packed into a chromatography column.

Testing of Mutant Probe Binding

Figure 13:
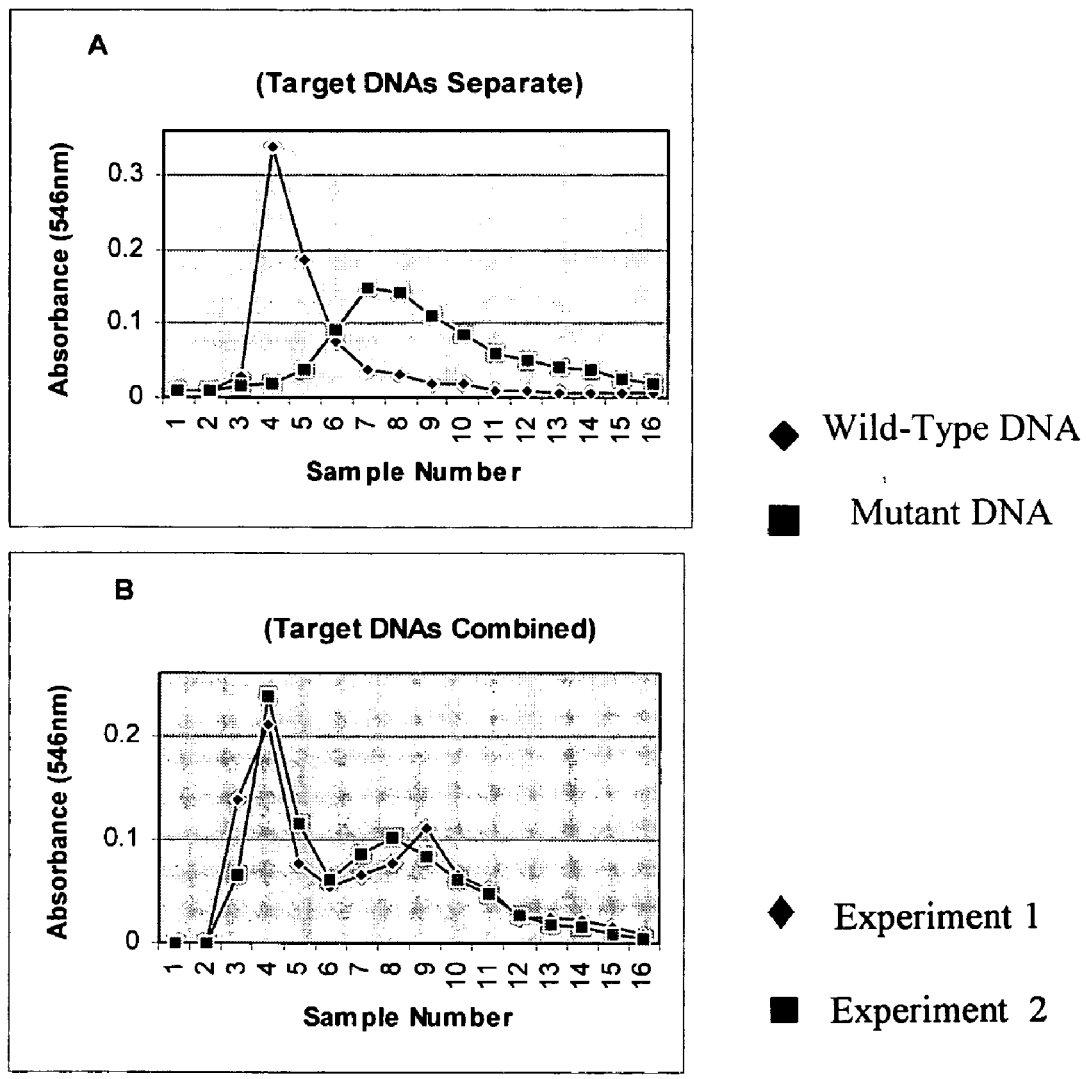
FIG. 13 shows the binding behavior of oligomers when using a column comprising mutant binding probes.

G6PD wild-type target DNA oligomer was loaded onto a column containing binding medium comprising mutant binding probes. Running buffer with 0.5% formamide (non-stringent running buffer) was flowed through the column. The wild-type target DNA oligomer was not recognized by the mutant binding probes and quickly passed through the column in a tight peak (FIG. 13A).

G6PD mutant target DNA oligomer was loaded onto a column containing binding medium comprising mutant binding probes. Running buffer with 0.5% formamide (non-stringent running buffer) was flowed through the column. The mutant target DNA oligomer was recognized and transiently bound by the mutant binding probes resulting in a peak shift (FIG. 13A).

G6PD mutant target DNA oligomer and G6PD wild-type target DNA oligomer were mixed together and loaded onto a column containing binding medium comprising mutant binding probes. Running buffer with 0.5% formamide (non-stringent running buffer) was flowed through the column. The expected double peak pattern was observed, indicating that the wild-type target DNA oligomer was not bound by the mutant binding probes and that the mutant target DNA oligomer was bound by the mutant binding probes (FIG. 13B).

Testing of Wild-Type Probe Binding

Figure 14:
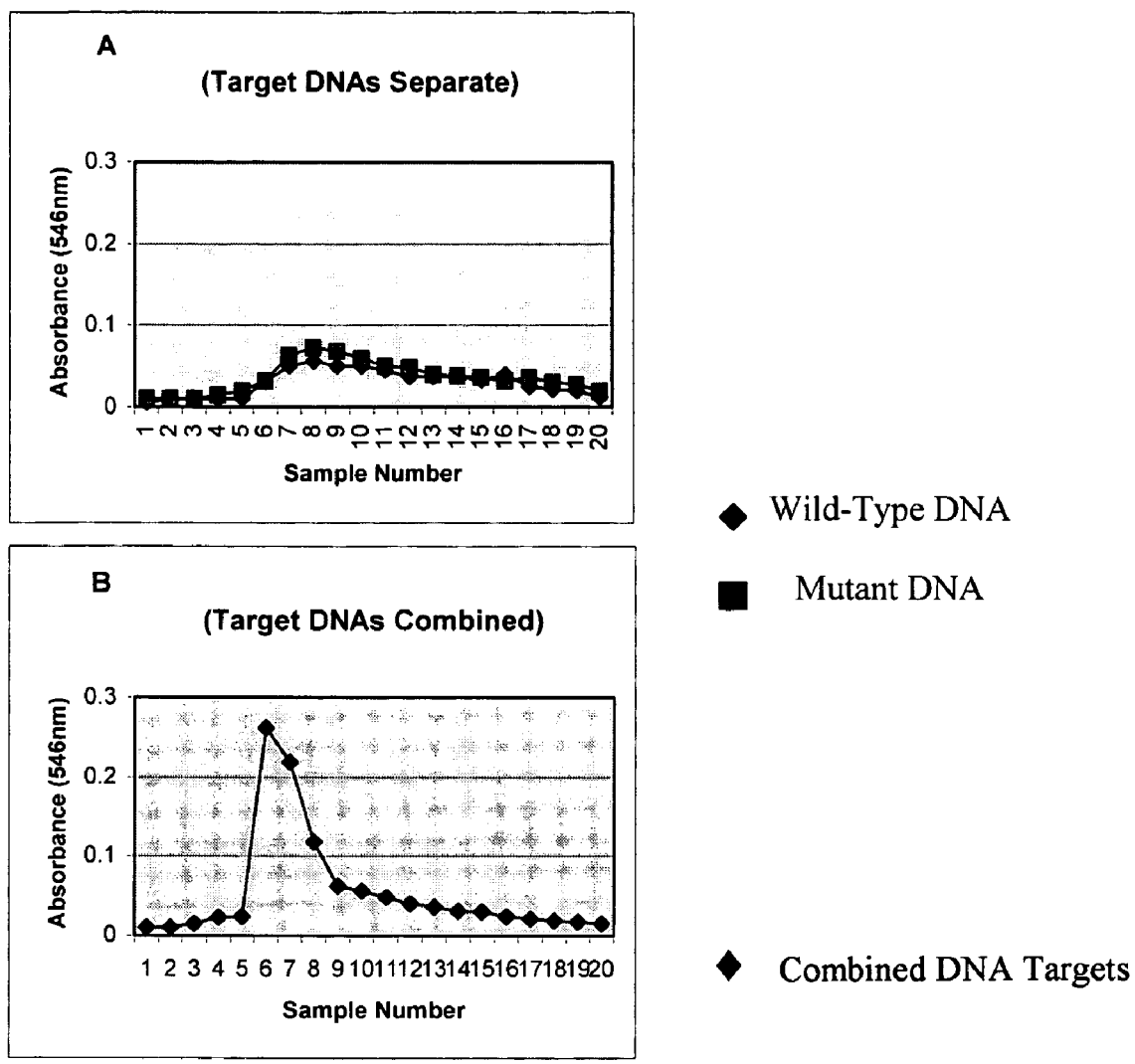
FIG. 14 shows the binding behavior of oligomers when using a column comprising wild type binding probes.

G6PD wild-type target DNA oligomer was loaded onto a column containing binding medium comprising wild-type binding probes. Running buffer with 0.5% formamide (non-stringent running buffer) was flowed through the column. The wild-type target DNA oligomer was recognized and transiently bound by the mutant binding probes resulting in a peak shift (FIG. 14A).

G6PD mutant target DNA oligomer was loaded onto a column containing binding medium comprising wild-type binding probes. Running buffer with 0.5% formamide (non-stringent running buffer) was flowed through the column. The mutant target DNA oligomer was recognized and transiently bound by the mutant binding probes resulting in a peak shift (FIG. 14A). The binding of the mutant target oligomer to the wild-type probe is due to a stable G-T mismatch.

G6PD mutant target DNA oligomer and G6PD wild-type target DNA oligomer were mixed together and loaded onto a column containing binding medium comprising wild-type binding probes. Running buffer with 0.5% formamide (non-stringent running buffer) was flowed through the column. The double peak pattern was not observed due to stable G-T mismatch binding of the mutant target oligomer. Instead a single shifted peak was observed (FIG. 14B).

Testing of Control Probe Binding

Figure 15:
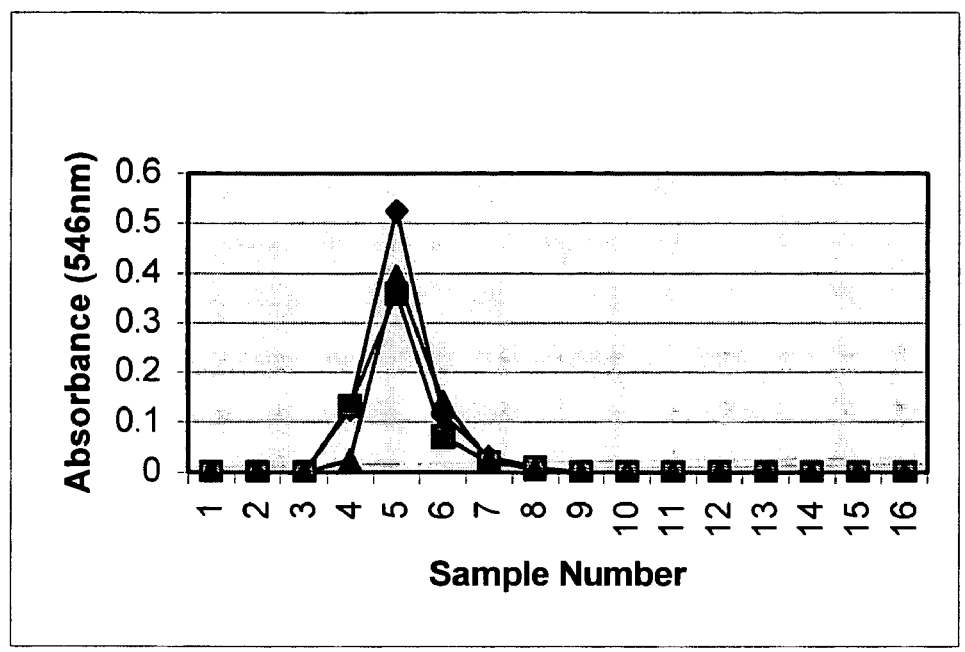
FIG. 15 shows the binding behavior of oligomers when using a column comprising control binding probes.

G6PD wild-type target DNA oligomer was loaded onto a column containing binding medium comprising control binding probes. Running buffer with 0.5% formamide (non-stringent running buffer) was flowed the column. The wild-type target DNA oligomer was not recognized and no peak shift was observed (FIG. 15).

G6PD mutant target DNA oligomer was loaded onto a column containing binding medium comprising control binding probes. Running buffer with 0.5% formamide (non-stringent running buffer) was flowed through the column. The wild-type target DNA oligomer was not recognized and no peak shift was observed (FIG. 15).

G6PD mutant target DNA oligomer and G6PD wild-type target DNA oligomer were mixed together and loaded onto a column containing binding medium comprising control binding probes. Running buffer with 0.5% formamide (non-stringent running buffer) was flowed through the column. Neither the wild-type target DNA oligomer nor the mutant target DNA oligomer was recognized and no peak shift was observed (FIG. 15).

Description of Terms Used

As used herein probes, probe oligomers, oligomer probes, DNA probes, RNA probes, nucleic acid probes, and probe nucleic acids refer to single stranded nucleic acid oligomers of a specific sequence that allows the probes to bind to at least a portion of a target oligomer.

As used herein the terms target oligomer, target oligomers, target nucleic acid sequences, target nucleic acid oligomers, target DNA sequences, target RNA sequences refer to oligonucleotide sequences present in the analyte. Target oligomers bind to at least a portion of probe oligomers.

As used herein oligomer or oligomers refers to RNA or DNA oligonucleotides, RNA or DNA oligonucleotide analogs, or a combination of RNA and/or DNA oligonucleotides and RNA and/or DNA oligonucleotide analogs. The RNA or DNA oligonucleotide analogs employed for the present invention can be oligomers in from one to all nucleotide subunits are replaced with a nucleotide analog to confer desired properties such as increased detectability, increased hybridization affinity, and resistance to degradation by a nuclease. Such oligonucleotide analogs include but are not limited to oligomers comprising 2'-O-alkyl ribonucleotides, phosphorothioate or methylphosphonate internucleotide linkages, locked nucleic acid oligomers, oligomers containing a 2'-O, 4'-C methylene bridge, peptide nucleic acid subunits, and nucleotides modified by attachment of radioactive atoms or groups, fluorescent groups, enzymes, chemiluminescent or bioluminescent molecules, groups which intercalate, cross-link or cleave a nucleic acid, or groups which alter the electric charge or hydrophobicity of the oligomers. Methods for making and using oligonucleotides and oligonucleotide analogs such as those listed above are well known to those skilled in the art of making and using sequence specific hybridizing oligomers.

As used herein detection refers to oligomer peak detection by ultraviolet, visible, fluorescent, infrared, colorimetric, bioluminescent, chemiluminescent, nuclear magnetic resonance, or radiometric detection.

As used herein alkyl refers to C1-C10 branched and unbranched hydrocarbon moieties, including hydrocarbon ring containing moieties.

As used herein subunits are the structural units of an oligomer, which bind to complementary subunits during hybridization. For example, for DNA and RNA oligonucleotides, the subunits are either the nucleotides joined together to form the oligomer or the bases attached to the backbone of the oligomer.

As used herein affinity chromatography is a method in which a sample containing target oligomers is allowed to move through a column or other container that contains a binding medium. Binding oligomers, also called probe oligomers, are present and are bound to solid support, forming the binding medium. Embodiments of the present invention utilize binding oligomers that are complementary to target oligomers of interest.

As used herein the terms mutation, mutate, mutated refer to nucleic acids and nucleic acid oligomers wherein one or more of the nucleotide bases present in the wild-type nucleic acid or nucleic acid oligomer have been changed through substitution or removal, as well as cases where a nucleotide has been added to the wild-type sequence.

As used herein labeled refers to oligomer that has been modified or labeled through the use of fluorescent molecules, bioluminescent molecules, chemiluminescent molecules, or radioactive atoms. Labeling may involve either covalent attachment or non-covalent attachment of label. Labeling is typically used to enhance the detection of the oligomer to which a label has been attached.

As used herein monolithic column refers to chromatography columns made of polymers containing large channels. The columns comprise aggregates of microglobules chemically linked to each other through crosslinks. The size of the large channels range from 2-5 µm. The backpressure of typical monolithic columns is similar to that of columns packed with 20-30 µm beads. However, the resolution of the monolithic columns is greater, equivalent to the resolution of high-pressure liquid chromatography columns packed with 5 µm beads.

We claim:

1. A method for identifying nucleic acid mutations comprising;
   obtaining a sample of target nucleic acid oligomers comprising at least one target sequence;
      where the target sequence is also known to exist in mutated form;
   dividing the sample into at least two parts;
   loading the parts onto at least two portions of binding medium;
      where each part is loaded onto a separate portion of binding medium;
      where the binding medium comprises probe nucleic acid oligomers bound to a solid support;
      where a first portion of binding medium comprises probe oligomers that are complementary to the at least one target sequence;
      where a second portion of binding medium comprises probe oligomers that are complementary to a mutated form of the at least one target sequence;
      where the rates of hybridization and dissociation of the target oligomers and the probe oligomers is about the same;
   flowing the oligomer-containing sample parts through the binding medium portions;
   detecting oligomer peaks in the fluid exiting from each of the at least two portions of binding medium;
   analyzing the oligomer peak data from the at least two portions of binding medium to identify the target nucleic acid oligomer mutations.

2. The method of claim 1 further comprising;
   dividing the sample into at least a third part;
   loading the at least a third part onto at least a third portion of binding medium;
   where the at least a third portion of binding medium comprises probe oligomers that are complementary to a sequence different from the at least one target sequence and differing from the mutated form of the at least one target sequence.

3. The method of claim 1 wherein the ratio of the rate of hybridization to the rate of dissociation is between about 35:65 and about 65:35.

4. The method of claim 1 further comprising the use of an internal standard.

5. The method of claim 1 where probe oligomers are covalently attached to the binding medium.

6. The method of claim 1 where probe oligomers are non-covalently attached to the binding medium.

7. The method of claim 1 where target oligomers comprise DNA.

8. The method of claim 1 where target oligomers further comprise a label.

9. The method of claim 1 where the at least one target sequence is associated with a human genetic disease.

10. The method of claim 9 where the disease is glucose-6-phosphate dehydrogenase deficiency.

11. The method of claim 9 where the disease is cystic fibrosis.

12. The method of claim 9 where the disease is muscular dystrophy.

13. The method of claim 9 where the disease is breast cancer.

14. The method of claim 9 where the disease is familial hypercholesterolemia.

15. The method of claim 9 where the disease is sickle cell anemia.

* * * * *